US00PP17646P2

(12) United States Plant Patent
Abrahamson et al.

(10) Patent No.: US PP17,646 P2
(45) Date of Patent: Apr. 24, 2007

(54) FAST-GROWING WILLOW SHRUB NAMED 'MILLBROOK'

(50) Latin Name: ***Salix purpurea*×*Salix miyabeana***
Varietal Denomination: Millbrook

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/244,636

(22) Filed: Oct. 6, 2005

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
*Assistant Examiner*—June Hwu
(74) *Attorney, Agent, or Firm*—Wall Marjama & Bilinski LLP

(57) ABSTRACT

A distinct female cultivar of *Salix purpurea*×*Salix miyabeana* named 'Millbrook', characterized by rapid stem growth producing 9% more woody biomass than one of its parents ('SX64') and 2% more biomass than a current production cultivar ('SV1'). 'Millbrook' produced greater than 2-fold more stem biomass than two other current production cultivars, 'SX67' and 'SX61'. 'Millbrook' can be planted from dormant stem cuttings, produces multiple stems after coppice, and the stem biomass can be harvested when the plant is dormant. In the spring following harvest, the plant will re-sprout very vigorously, producing new stems that can be harvested after two to four years of growth. This harvest cycle can be repeated several times. The stem biomass can be chipped and burned as a source of renewable energy, generating heat and/or electricity. 'Millbrook' displays a low incidence of rust disease.

10 Drawing Sheets

CROSS-REFERENCE TO RELATED APPLICATIONS

This application is related to the following plant patent applications, all of which are subject to assignment to the Research Foundation of the State University of New York, and each of which is being filed on even date herewith: "Fast-Growing Shrub Willow" Named 'Fish Creek', application Ser. No. 11/244,988, "Fast-Growing Shrub Willow" Named 'Canastota', application Ser. No. 11/244,986, "Fast-Growing Shrub Willow" Named 'Oneida', application Ser. No. 11/244,975 "Fast-Growing Shrub Willow" Named 'Otisco', application Ser. No. 11/244,987 "Fast-Growing Shrub Willow" Named 'Owasco', application Ser. No. 11/244,842 and "Fast-Growing Shrub Willow" Named 'Tully Champion', application Ser. No. 11/244,635. The variety of fast-growing shrub willow named 'Millbrook' was produced in the same willow breeding program as were other varieties, including: 'Fish Creek', 'Canastota', 'Oneida', 'Otisco', 'Owasco', and 'Tully Champion'.

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

BACKGROUND OF THE INVENTION

1. Field of the Invention

The invention is a new and distinct cultivar known by the varietal name 'Millbrook' resulting from the novel hybridization of *Salix purpurea* with *Salix miyabeana*. The new variety was produced through controlled willow breeding conducted by the inventors in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow is being developed as an agricultural crop plant that will be grown and harvested as a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed Under 37 CFR 1.97–1.99.

This new variety of *Salix purpurea*×*Salix miyabeana* was the seedling progeny of the controlled pollination of the female clone *Salix purpurea* '95026' by the male clone *Salix miyabeana* 'SX64' performed in February 1999 in Syracuse, N.Y. The plant has been propagated repeatedly by stem cuttings and has been found to retain its distinctive characteristics through successive propagations and field trials. More specifically, the plant has been asexually reproduced by collecting dormant stems during winter months, cutting them into either 5 inch or 10 inch pieces (cuttings), then planting those cuttings in the field in the spring or in potting mix in a greenhouse, then transplanting the rooted cuttings to the field.

The female parent, *Salix purpurea* '95026' was originally identified in 1995 growing on the shore of a creek in Dutchess County, N.Y. and was vegetatively propagated from stem cuttings. This female parent, clone *Salix purpurea* '95026', is distinguished by opposite leaves that are obovate with entire margins. The variety 'Millbrook' has alternate 'SX64' was originally transferred from Toronto, Ontario, Canada, to Syracuse, N.Y. in 1994 and was vegetatively propagated from stem cuttings in Syracuse, N.Y. The growth of the parent plants was characterized in nursery plantings. Both parents displayed rapid stem growth and low incidence of disease, so were chosen to serve as parents in a cross. The seedlings produced by this cross (identification #99217) were first established in a greenhouse, and then were transplanted to a field in Syracuse, N.Y. This particular individual (identification #99217-015) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately three years.

SUMMARY OF THE INVENTION

The *Salix purpurea*×*Salix miyabeana* cultivar 'Millbrook' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Millbrook'. These characteristics in combination distinguish 'Millbrook' as a new and distinct cultivar:

1. Rapid growth rate, producing 9% more woody biomass than one of its parents (*Salix miyabeana* 'SX64'), 2% more biomass than one current production cultivar (*Salix dasyclados* 'SV1'), and more than 2-fold more biomass than two other production cultivars (*Salix miyabeana* 'SX67' and *Salix sachalinensis* 'SX61') when grown in the same field for the same length of time (two growing seasons after coppice) in Tully, N.Y.
2. Low incidence of rust disease assessed in experimental trials conducted in Syracuse, N.Y. in 2000.

BRIEF DESCRIPTION OF THE DRAWING

The accompanying color photographs show the features of the claimed cultivar in a manner as true as is reasonably possible. The illustrations include:

FIG. 1.1 illustrates two-year old portion of stem collected while dormant;

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in soil:sand in a greenhouse;

FIG. 1.6 illustrates upper leaf surface;

FIG. 1.7 illustrates lower leaf surface;

FIG. 1.8 illustrates mature catkin; and

FIG. 1.9 illustrates pistil and densely pubescent floral bract.

FIG. 2.1 illustrates the biomass yield two years after coppice in Tully, N.Y. as compared to other shrub willows.

DETAILED DESCRIPTION OF THE NEW PLANT

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter The R.H.S. Colour Chart) of The Royal Horticultural Society of London, England, except where general terms of ordinary dictionary significance are used.

BOTANICAL DESCRIPTION OF THE PLANT

The following detailed description of the 'Millbrook' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes every 2 hours five times each day.

Latin name: *Salix purpurea*×*S. miyabeana.*
Varietal denomination: 'Millbrook'.
Parentage:
*Female or seed parent.*—*S. purpurea* '95026'.
*Male or pollen parent.*—*S. miyabeana* 'SX64'.
Propagation:
*Type.*—Stem cuttings.
*Time to rooting.*—Approximately 10 days in water at 21° C.
Precocity: Subprecocious — Catkins mature as leaves begin to break bud.
Plant description: The color of one-year-old stem cuttings observed when dormant are grey orange (RHS 164C, RHS171A), while two- to three-year-old stems are yellow-green to pale green (RHS 153A, RHS 148D) and lustrous. Vegetative buds are red-orange (RHS 180A), deltate, and typically 4 mm in length. Lenticels are large, brown, and sparse. The leaves are simple and alternate with pinnate venation. Petioles are typically 3 mm in length and yellow-green (151D). Stipules are typically 1 mm in length, ovate, and yellow-green (144A). Pistils, as shown in the drawings, are typically 1 mm in length. Immature leaves have very few hairs. Mature leaves are slightly oblanceolate, acute apex, acute-obtuse base, typically 8.1–8.8 cm in length, 1.5–1.9 cm in width, serrate margin, adaxial (upper) surface green (144A), abaxial (lower) surface light pale green (143D), and stem light green (RHS 144C) at 6 weeks of growth. The upper surface of the leaves is glabrous, smooth, and slightly glaucous. The lower surface of the leaves is glabrous, very light glaucous to glossy, with apparent venation.

The average diameter of two-year old stems at a height of 1 m is 1.1 cm. The bark color of two-year old field-grown stems is yellow-green (152A). The surface is slightly rough with shallow longitudinal furrows.

The average plant height of a mature plant after three seasons of growth is 5–6 m, with a spread of 1.5–2.0 m in the typical planting spacing of 0.5 m×0.6 m.

Flowering description: Dormant floral buds are elongated, ovoid, acute, typically 9.5 mm in length, slightly raised, and red (RHS 179A). Yellow-green (146A) peduncle of catkin is typically 3.5 mm in length and bears 4–5 leafy bracts. Catkins are curved 90°, typically 2.6–3.0 mm in length, and narrowly cylindrical. Flowers have a short, round, sessile ovary with short soft hairs, a very short style, and 2 broad stigmas. Floral bract is densely hairy with a pink obtuse apex.

Field growth characteristics: Determined through surveys of plants growing in the field in Tully, N.Y. and in Syracuse, N.Y.

Disease resistance: Displays a low incidence of rust disease.

Temperature tolerance: Stems typically do not suffer frost damage at temperatures as low as 10° F. and may suffer only minor tip dieback at lower temperatures.

Seed production: 'Millbrook' produces only female flowers, so viable seeds will only be produced after pollination by a compatible male variety. This has not yet been observed in field trials.

Biomass yield: Mean dry stem biomass yield produced through two growing seasons after coppice in each of eight four-plant plots ('Millbrook', 11.30 oven dry tons $ha^{-1}$ $yr^{-1}$) measured in a yield trial growing in Tully, N.Y. in February 2005 was 9% greater than the mean stem biomass yield of one of its parents ('SX64', 10.35 oven dry tons $ha^{-1}$ $yr^{-1}$) and was 2% greater than a current production cultivar ('SV1', 11.04 oven dry tons $ha^{-1}$ $yr^{-1}$) growing in the same trial (FIG. 2.1). 'Millbrook' produced greater than 2-fold more stem biomass than two other current production cultivars ('SX67', 5.52 oven dry tons $ha^{-1}$ $yr^{-1}$; 'SX61', 4.83 oven dry tons $ha^{-1}$ $yr^{-1}$) growing in the same trial (FIG. 2.1).

What is claimed is:

1. A new and distinct variety of *Salix purpurea*×*Salix miyabeana* plant, substantially as illustrated and described herein.

* * * * *

Fig. 1.1
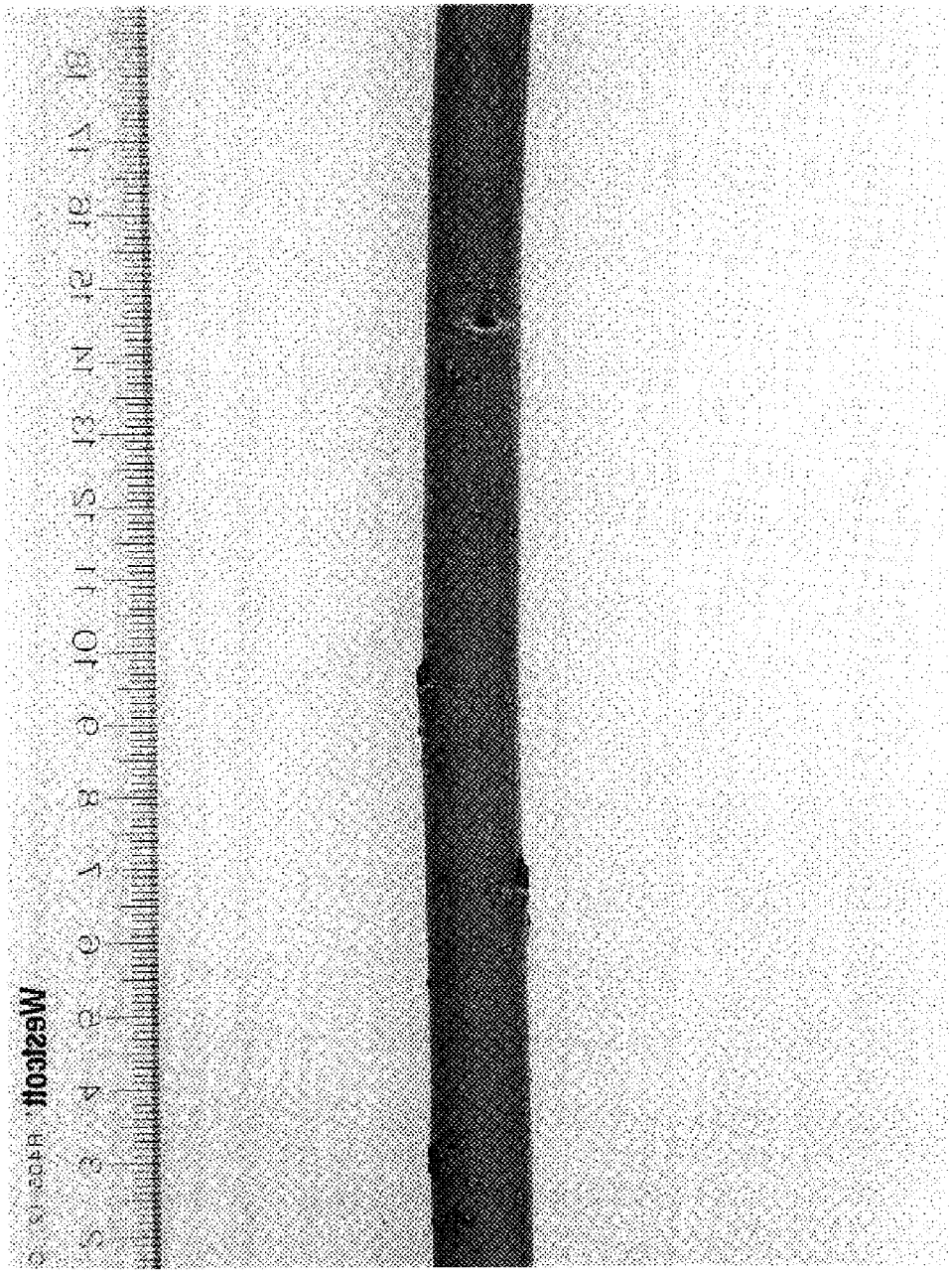

Fig. 1.2
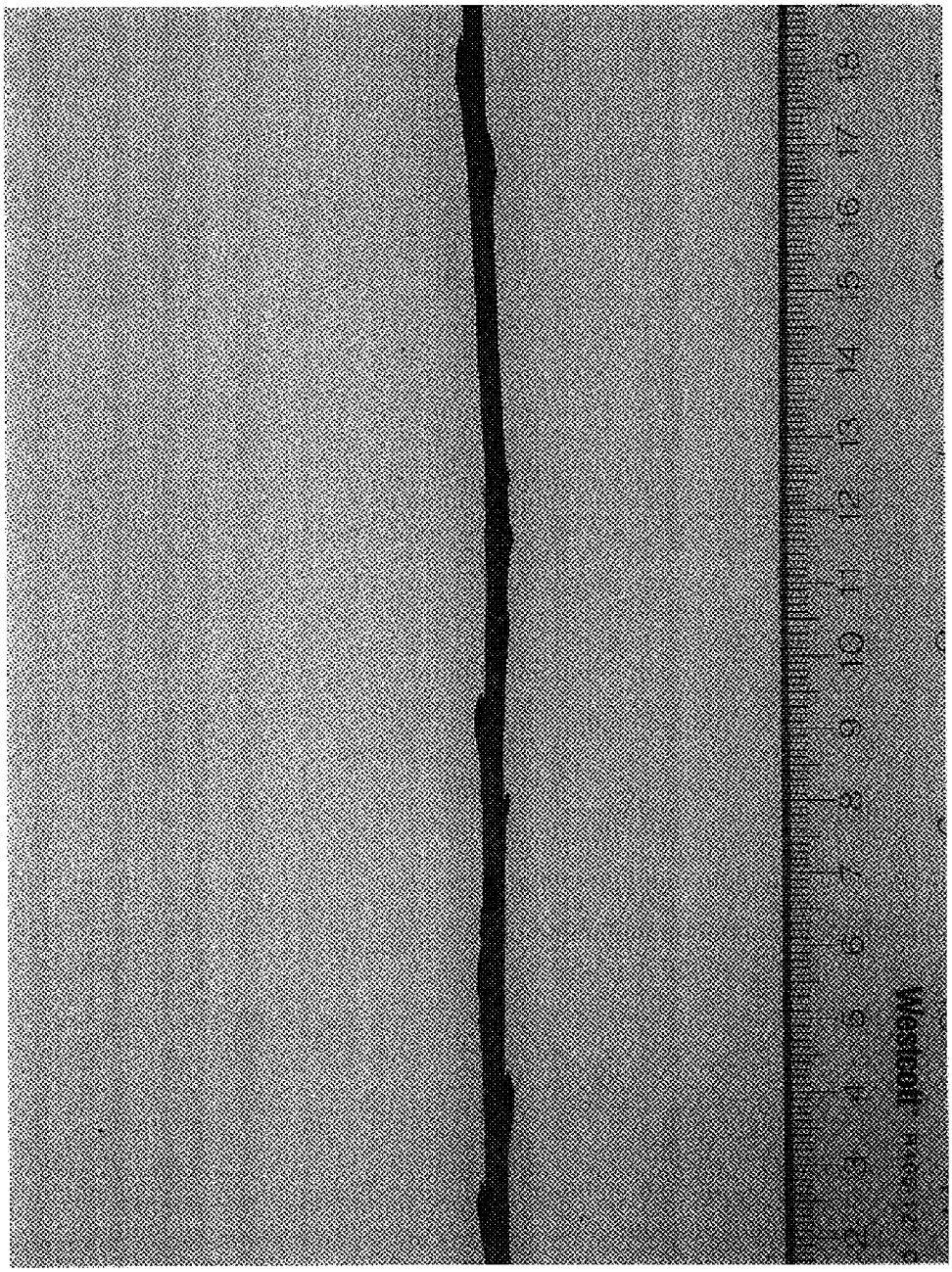

Fig. 1.3
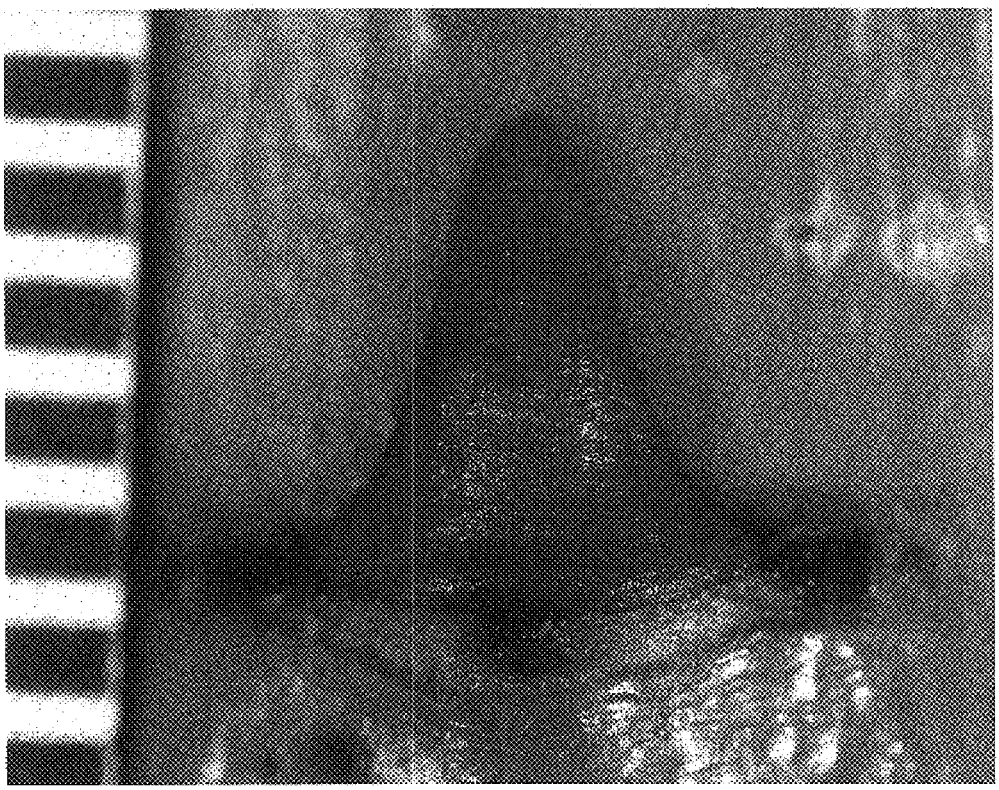

Fig. 1.4
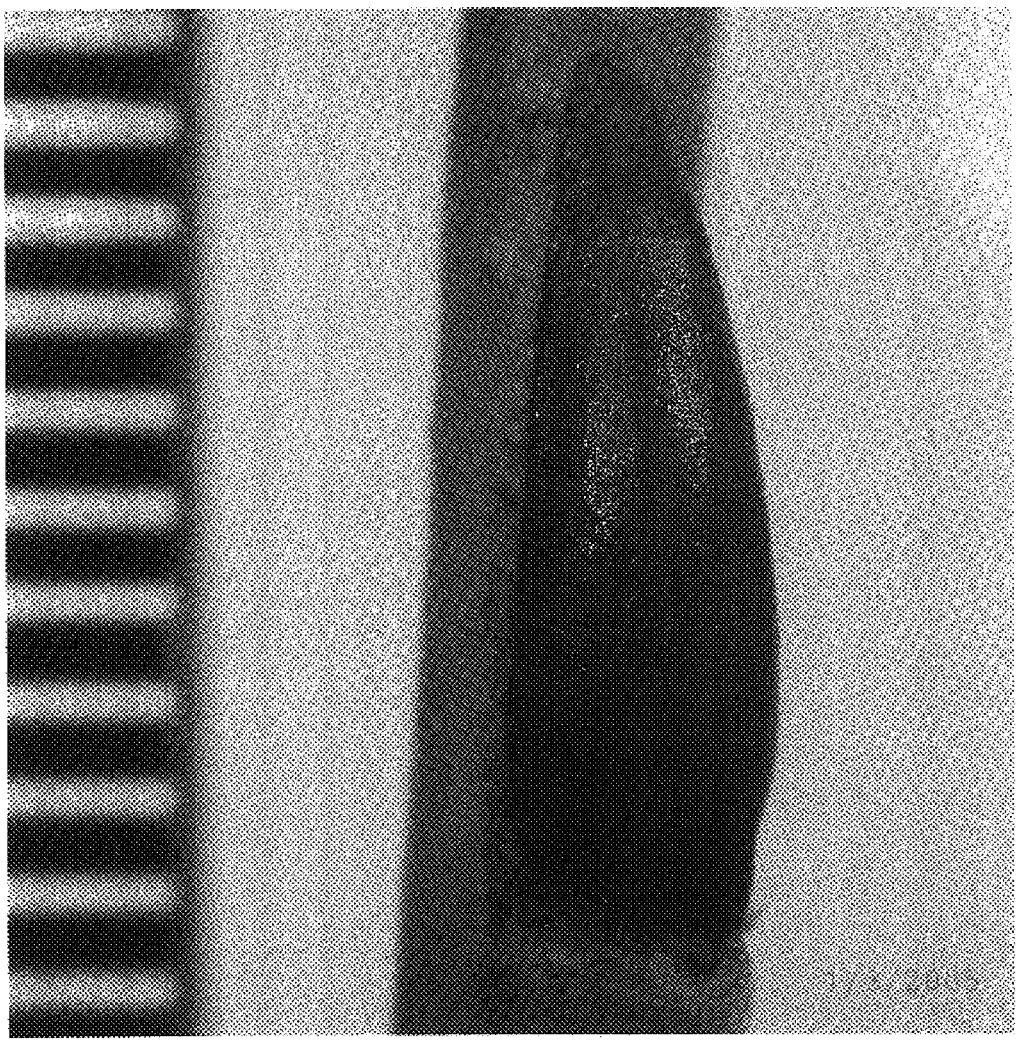

Fig. 1.5
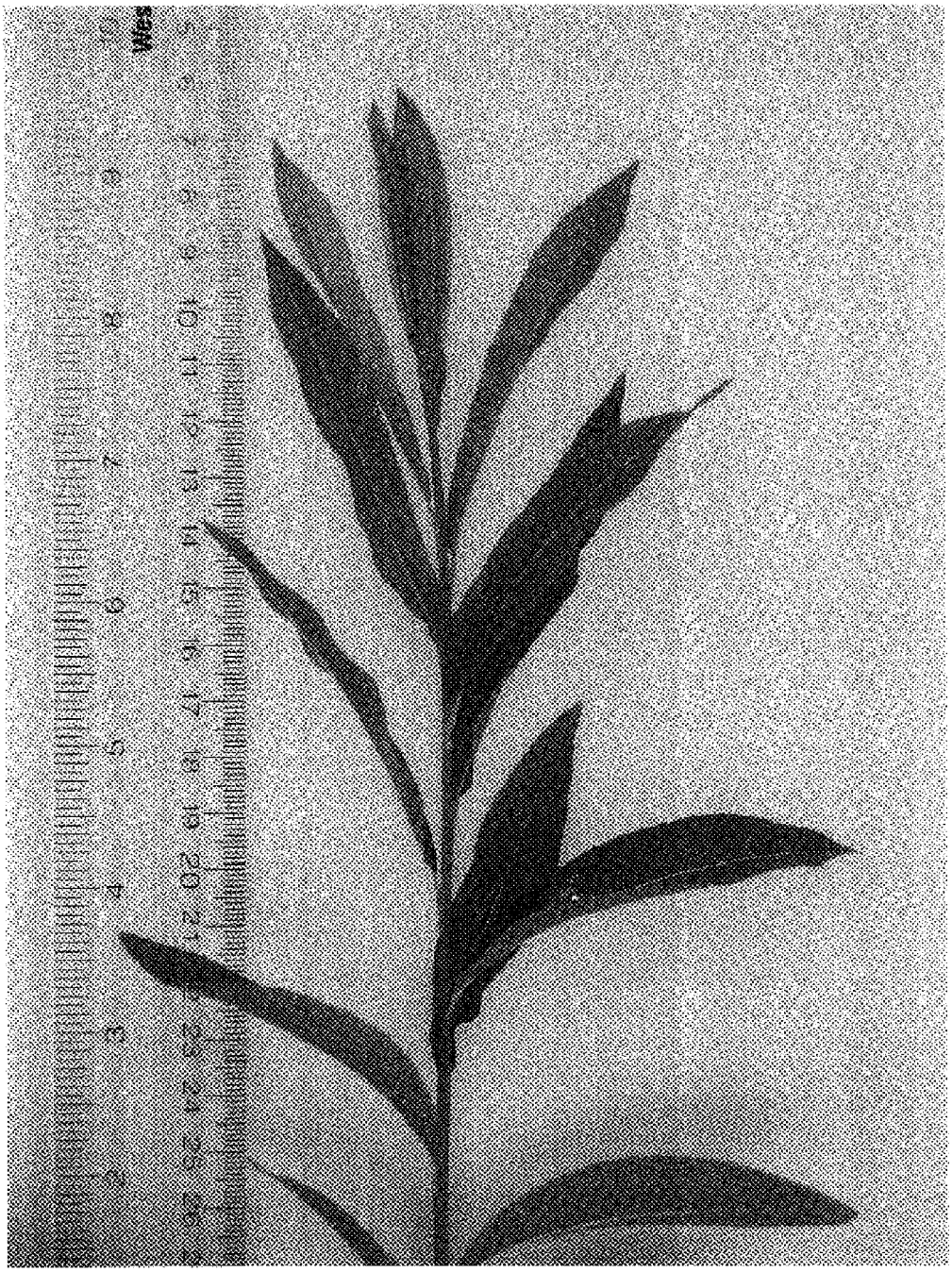

Fig. 1.6
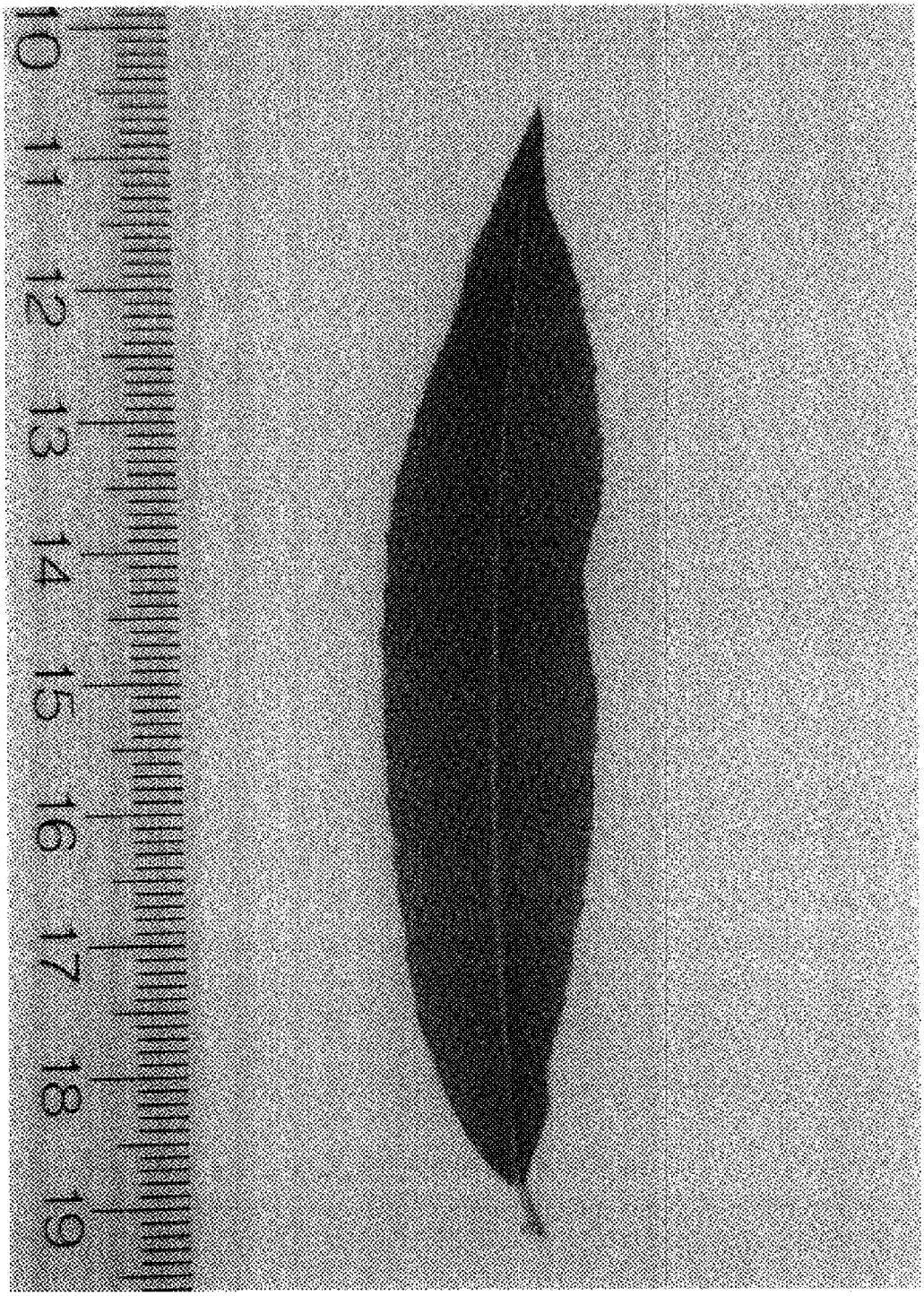

Fig. 1.7
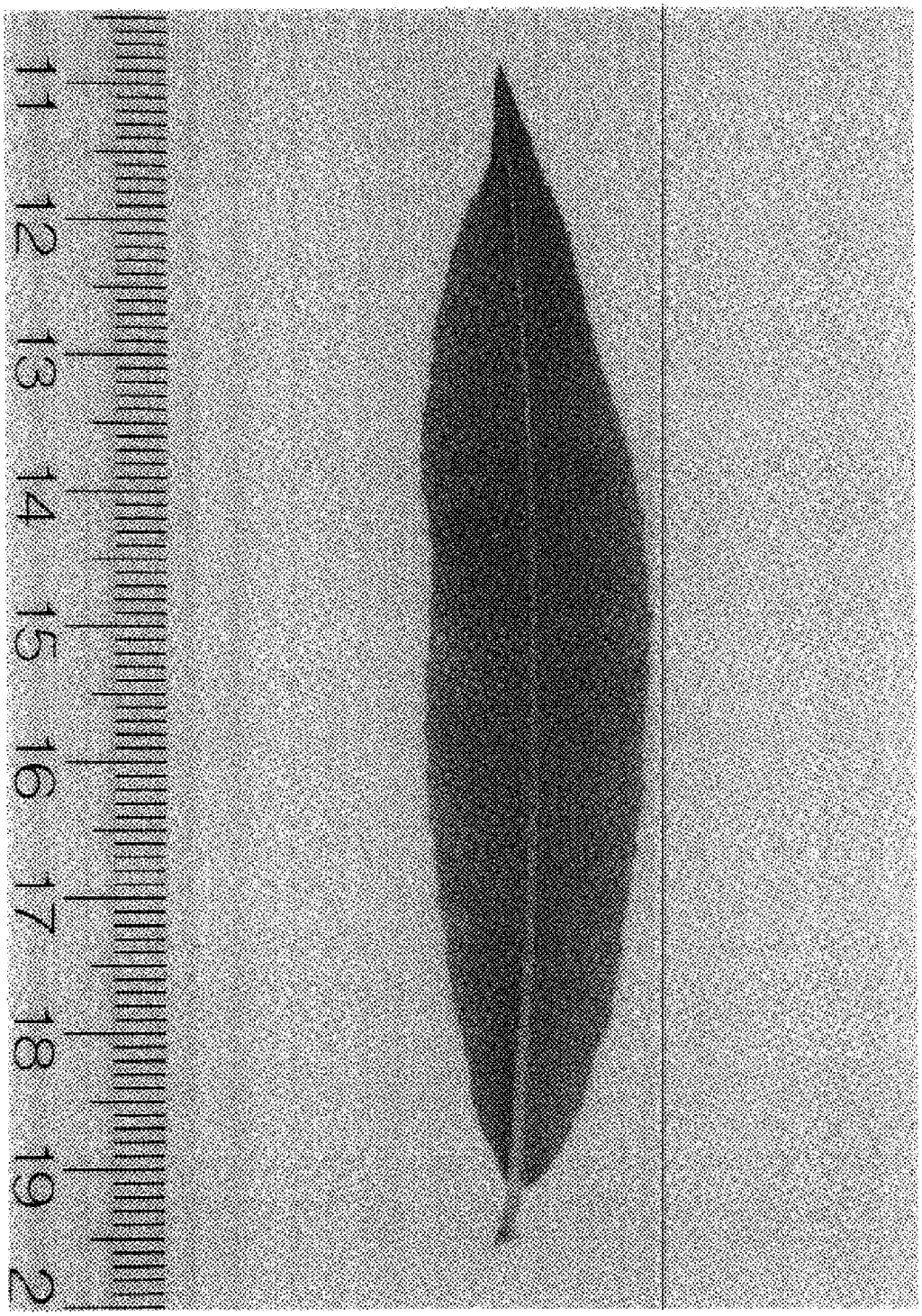

Fig. 1.8
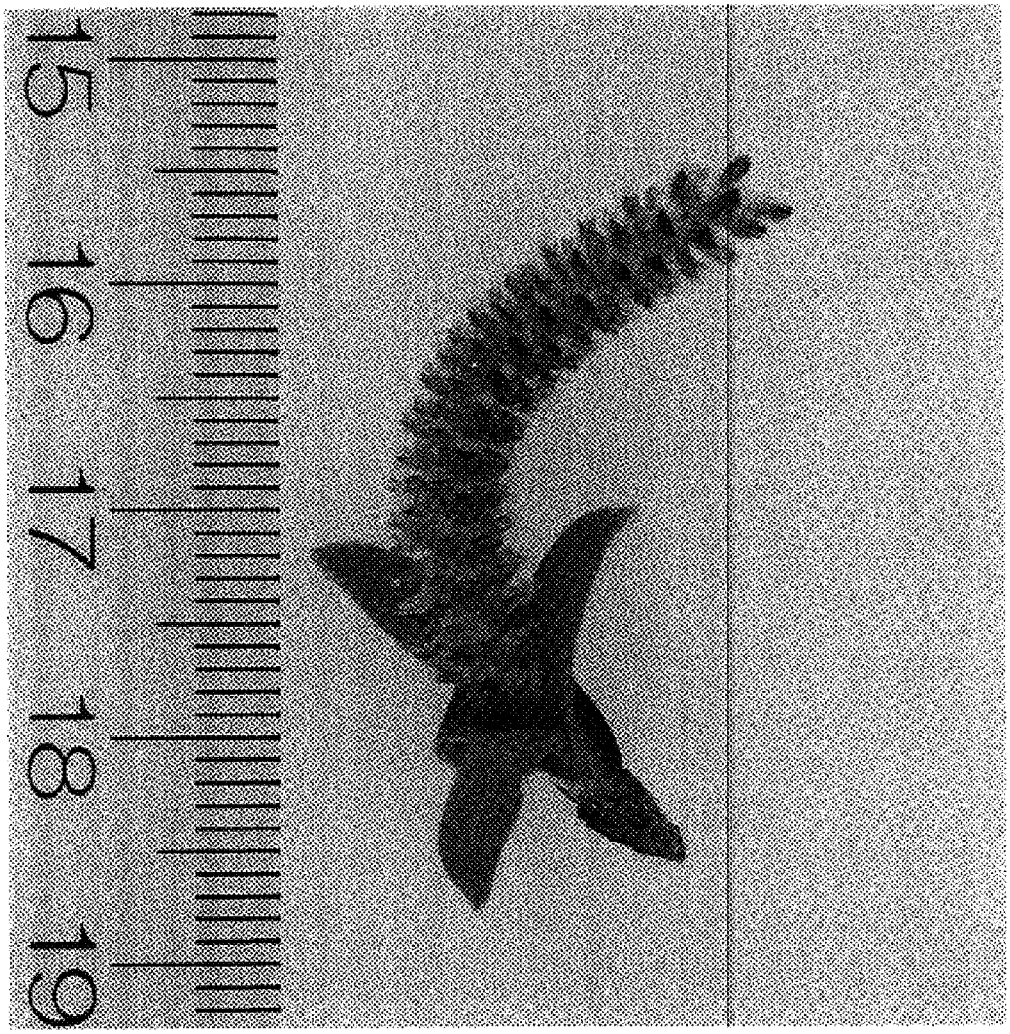

Fig. 1.9
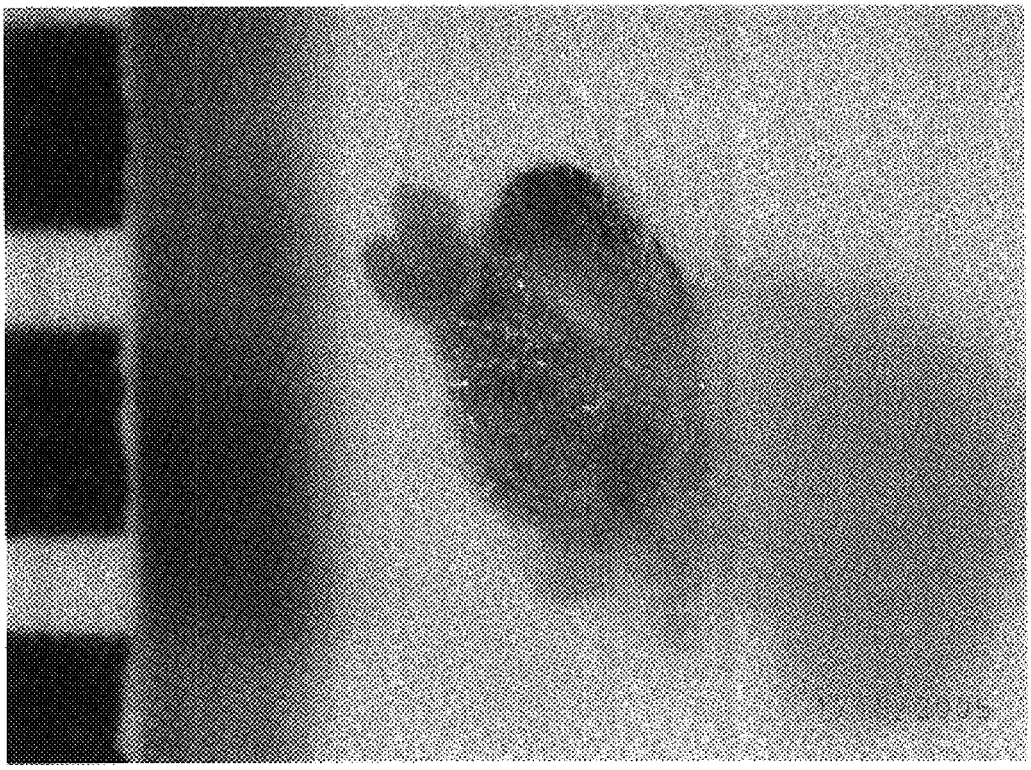

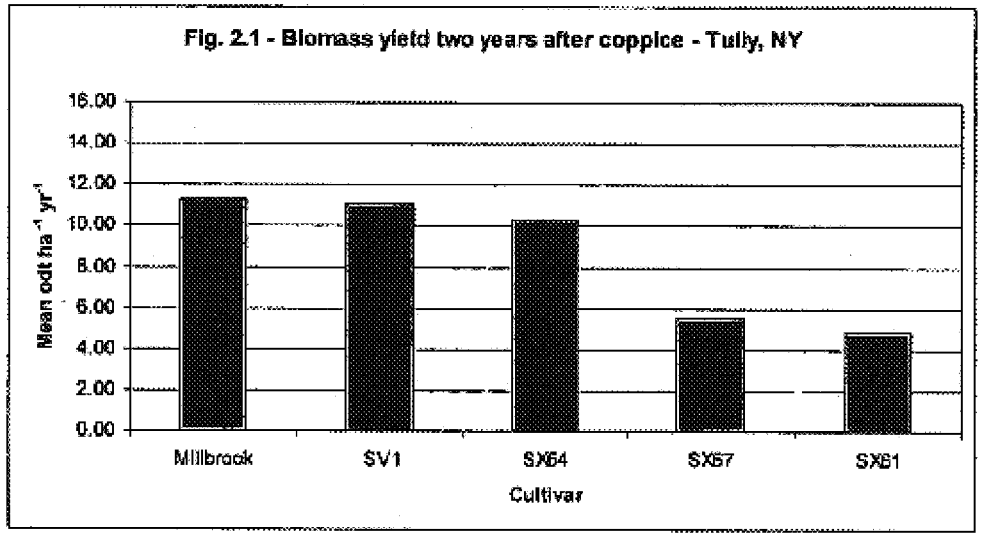
Fig. 2.1 - Biomass yield two years after coppice - Tully, NY
16.00
14.00
12.00
10.00
8.00
6.00
4.00
2.00
0.00
Mean odt ha-1 yr-1
Millbrook
SV1
SX64
SX67
SX61
Cultivar

UNITED STATES PATENT AND TRADEMARK OFFICE

CERTIFICATE OF CORRECTION

PATENT NO. : PP 17,646 P2
APPLICATION NO. : 11/244636
DATED : April 24, 2007
INVENTOR(S) : Lawrence P. Abrahamson et al.

It is certified that error appears in the above-identified patent and that said Letters Patent is hereby corrected as shown below:

On Title Page 1, Before the words "10 Drawing Sheets", insert -- 1 Claim --;

Signed and Sealed this

Seventeenth Day of July, 2007

JON W. DUDAS
*Director of the United States Patent and Trademark Office*